United States Patent [19]
Mehl, Sr.

[11] Patent Number: 5,868,738
[45] Date of Patent: Feb. 9, 1999

[54] METHOD AND APPARATUS FOR PERMANENT REMOVAL OF MULTIPLE HAIRS WITH A HAIR CLAMPING COMB

[76] Inventor: Thomas L. Mehl, Sr., 1015 Highway 337, Old Bronson Rd., Newberry, Fla. 32669

[21] Appl. No.: 573,642

[22] Filed: Dec. 18, 1995

Related U.S. Application Data

[63] Continuation-in-part of PCT/US94/14557, Dec. 30, 1994, which-is-a continuation-in-part of Ser. No. 176,561, Dec. 30, 1993, Pat. No. 5,470,332, which is a continuation-in-part of Ser. No. 917,662, Jul. 20, 1992, abandoned, which is a continuation of Ser. No. 794,364, Nov. 13, 1991, abandoned, which is a continuation of Ser. No. 454,622, Dec. 21, 1989, abandoned, which is a continuation-in-part of Ser. No. 66,261, May 25, 1993, abandoned, which is a continuation-in-part of Ser. No. 929,750, Aug. 17, 1992, abandoned, which is a continuation-in-part of Ser. No. 707,828, May 30, 1991, abandoned.

[51] Int. Cl.[6] ................................................. A61B 17/41
[52] U.S. Cl. .............................................. 606/36; 606/43
[58] Field of Search ................ 606/36, 43; 219/222–225

[56] References Cited

U.S. PATENT DOCUMENTS

| 4,274,413 | 6/1981 | Hahn et al. | 606/43 |
| 5,470,332 | 11/1995 | Mehl, Sr. et al. | 606/36 |

*Primary Examiner*—Lee S. Cohen
*Attorney, Agent, or Firm*—Shlesinger, Arkwright & Garvey LLP

[57] ABSTRACT

A method of removing multiple hairs and inhibiting future hair growth includes the steps of applying a conductive solution to the hair, applying power for a period of time sufficient to destroy the matrix area of the hair, and allowing the treated hair to either be removed immediately or to stay in the skin for a period of time sufficient for the chemical reaction induced at the matrix area to continue long enough to destroy the matrix area and prevent regrowth of the hair. The power may be applied through a conductive element of a comb. The comb is configured for carrying out the method. The comb may be provided with a moveable clamp for treating hair. The movable clamp may likewise be used to grasp and to remove treated hair when the grasped/clamped treated hair is moved relative to the skin by movement of the comb.

20 Claims, 9 Drawing Sheets

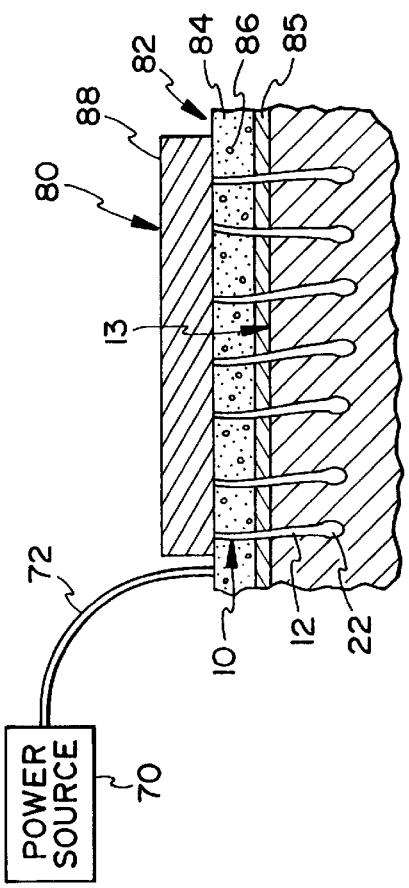
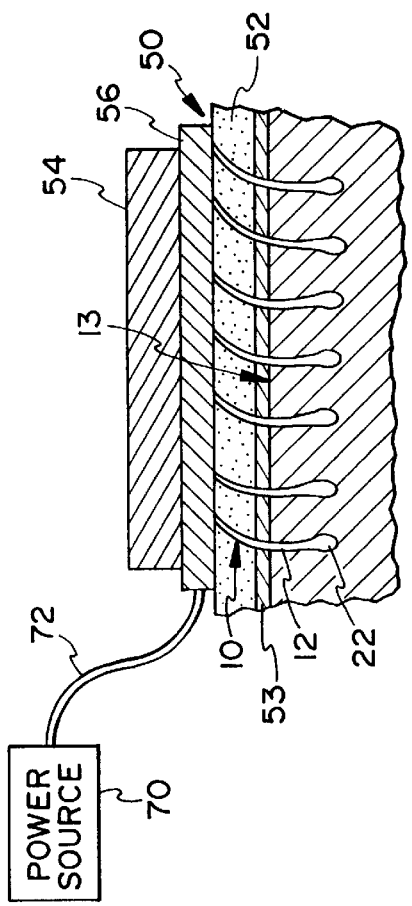
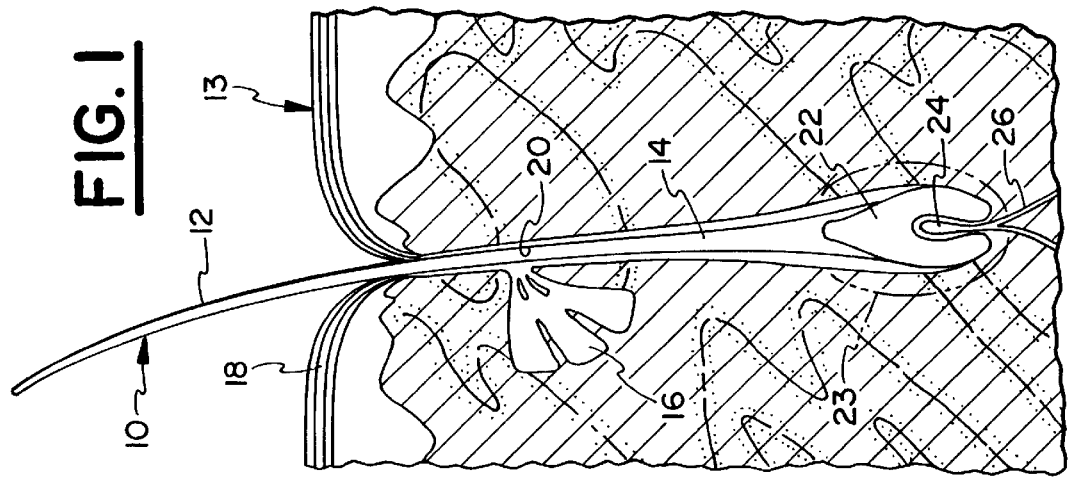

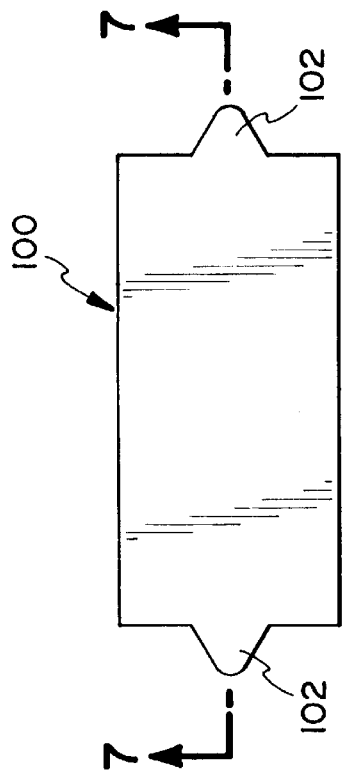
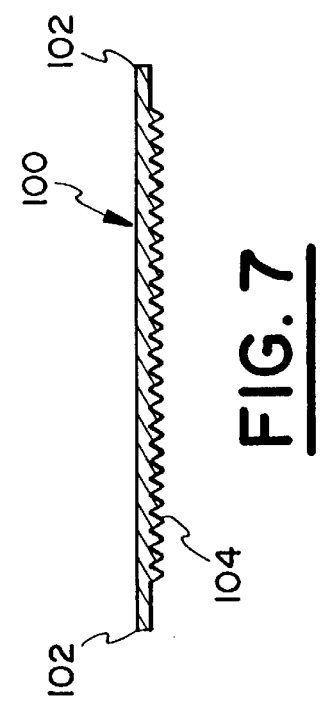
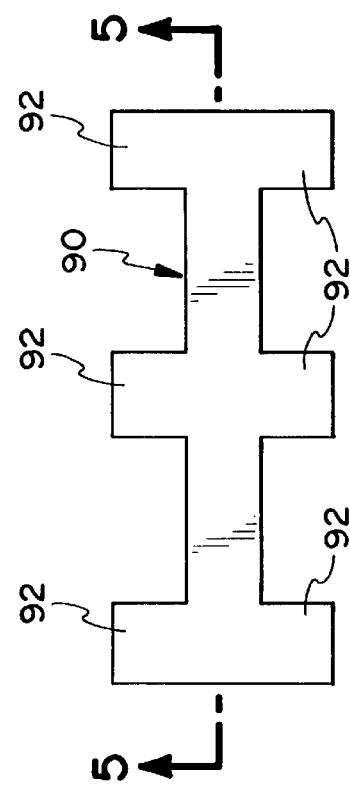
FIG. 6
FIG. 8
FIG. 7
FIG. 4
FIG. 5

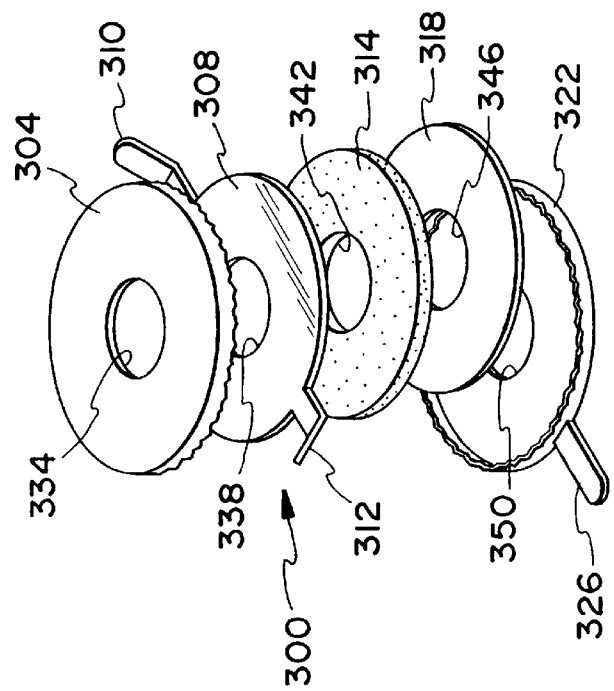
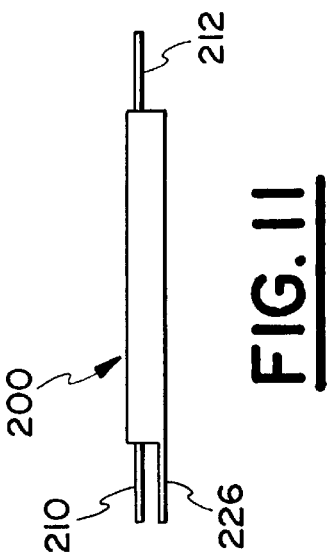
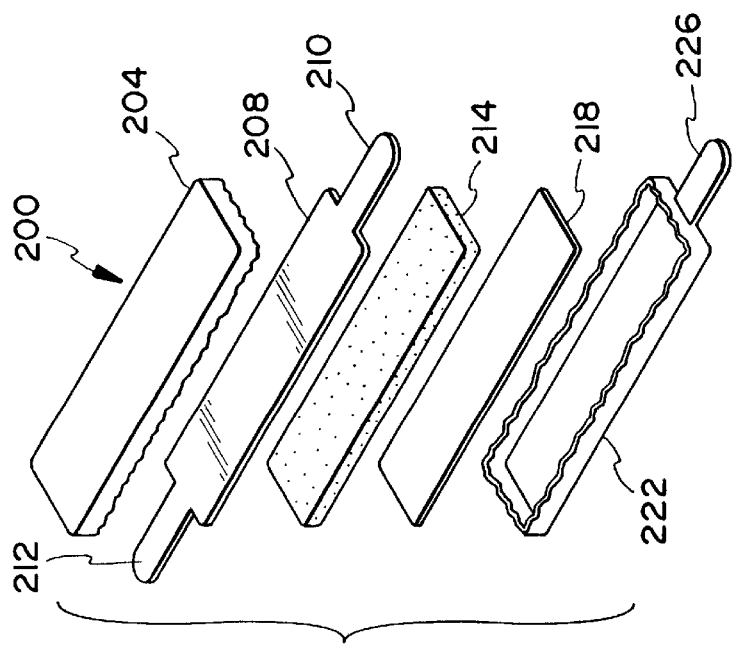
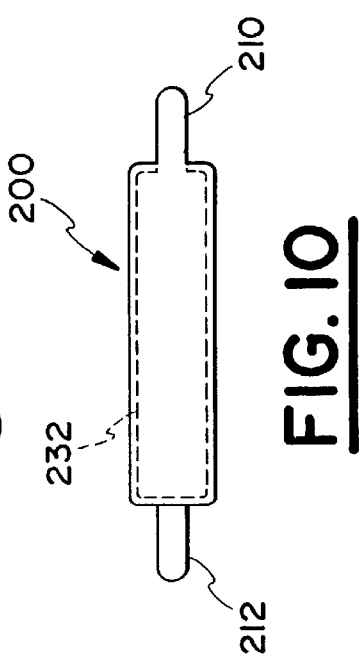
FIG. 12
FIG. 11
FIG. 10
FIG. 9

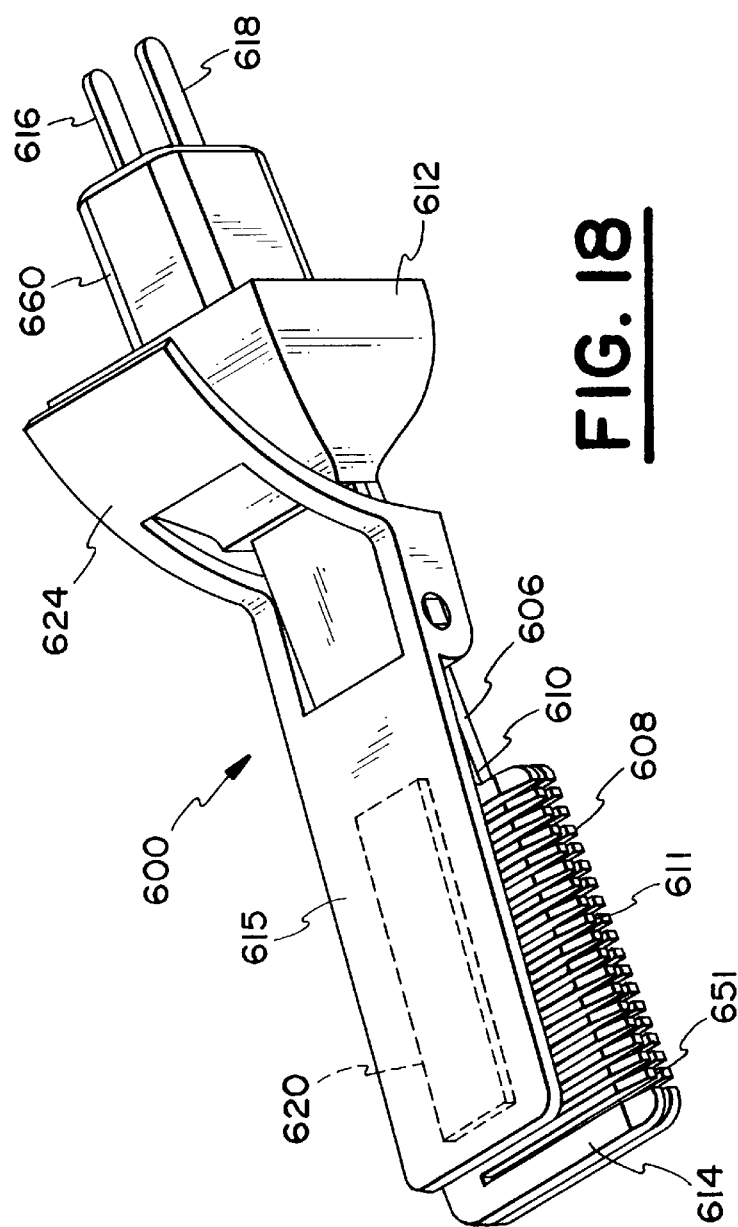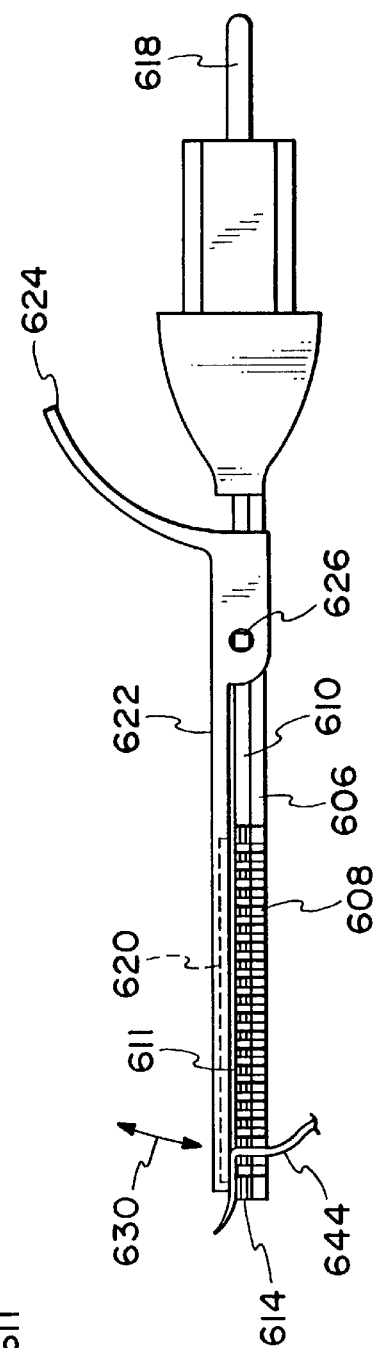

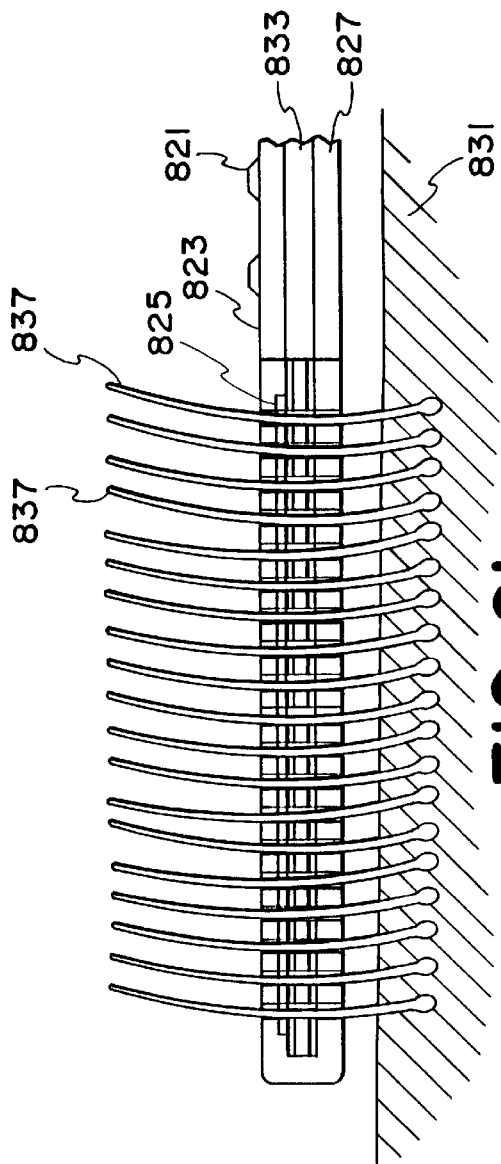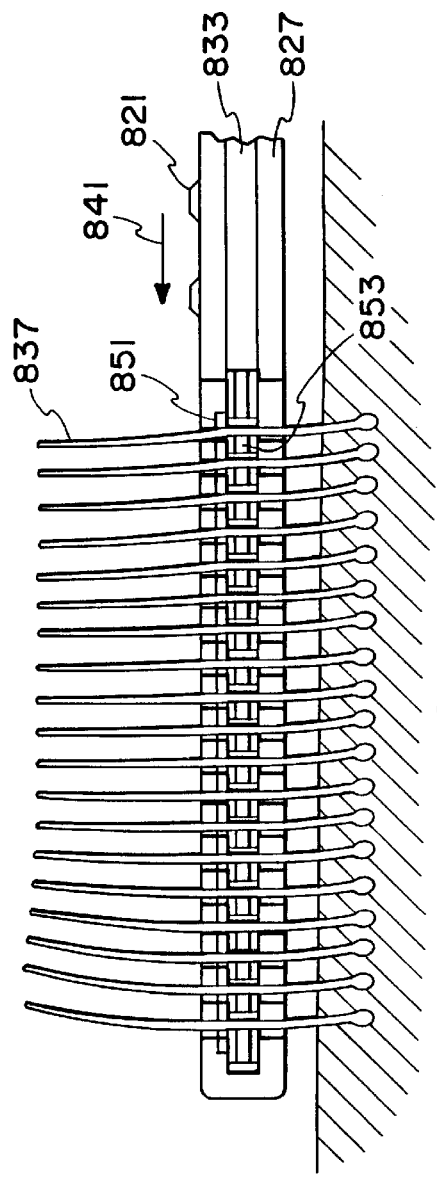

METHOD AND APPARATUS FOR PERMANENT REMOVAL OF MULTIPLE HAIRS WITH A HAIR CLAMPING COMB

CROSS REFERENCE TO RELATED APPLICATIONS

This application is a continuation-in-part of application Ser. No. PCT/US94/14557, filed Dec. 30, 1994, which is a continuation-in-part of application Ser. No. 08/176,561, filed Dec. 30, 1993, now U.S. Pat. No. 5,470,332, which is a continuation-in-part of application Ser. No. 07/917,662, filed Jul. 20, 1992, now abandoned, which is a continuation of application Ser. No. 07/794,364, filed Nov. 13, 1991, now abandoned, which is a continuation of application Ser. No. 07/454,622, filed Dec. 21, 1989, now abandoned, which is a continuation-in-part of application Ser. No. 08/066,261, filed May 25, 1993, now abandoned, which is a continuation-in-part of application Ser. No. 07/929,750, filed Aug. 17, 1992, now abandoned, which is a continuation-in-part of application Ser. No. 07/707,828, filed May 30, 1991, now abandoned, each of which is incorporated herein by reference.

FIELD OF THE INVENTION

This invention relates to a method for removing hair and for permanently impairing future hair growth, and an apparatus for carrying out this method.

BACKGROUND OF THE INVENTION

Inventors have long sought to permanently remove unwanted hair. Known techniques for hair removal are described in patents such as the following.

U.S. Pat. No. 5,364,394 to Mehl, which issued Nov. 15, 1994, is a continuation of U.S. patent application Ser. No. 08/140,336, filed Oct. 21, 1993, which was a continuation of U.S. patent application Ser. No. 07/917,662, referred to above, discloses a radio frequency (RF) hair removal method which effectively and permanently impairs future hair regrowth.

U.S. Pat. No. 4,174,714 to Mehl discloses a method for permanent removal of hair in which hair is removed and future hair growth is permanently impaired by grasping reduced lengths of a hair between conductive hair engaging surfaces, applying high frequency electrical waves to one of the conductive hair engaging surfaces, and holding the hair engaging surfaces in firm engagement in position against the skin and hair while applying the high frequency electrical waves until the hair releases. Although this method works well, there is a need for an even more efficient method of permanent hair removal.

U.S. Pat. No. 5,026,369 to Cole discloses a non-invasive method of removing hair through electrolysis in which a particular hair to be removed is cleaned, and then bathed in an electrode solution. A conductor is attached to a remote end of the treated hair after which a DC electrical current is directed down the electrode solution coating outside of the hair to the soft moist tissue surrounding hair within the skin, whereby sodium hydroxide (NaOH) in the hair follicle site is produced owing to the chemical reaction in the presence of electrical current for causing the hair follicle to die and allow the hair associated with the dead hair follicle to be removed.

U.S. Pat. No. 5,049,148 to Mehl discloses a radio frequency hair removal tweezer including tweezer arms having facing interior surfaces including a radio frequency conducting hair engaging metal conducting pad for grasping hair to be removed. Although this hair removal tweezer operates well, there is a need for an effective hair removal method and apparatus which is even simpler and easier to use.

OBJECTS AND SUMMARY OF THE INVENTION

Accordingly, it is an object of the invention to provide a multiple hair removal method and apparatus for carrying out the method that are simpler to perform and to use than the known methods and apparatus.

It is another object of the invention to provide a hair removal method, system, and apparatus suited for removing multiple hairs at one time.

It is a further object of the invention to remove multiple hairs easier and faster without stress and infection.

It is a still further object of the invention to provide a method and apparatus for permanent hair removal and impairment of hair regrowth.

It is an additional object of the invention to provide a hair removal system which has few or no moving parts.

It is a further object of the invention to provide a hair removal system which is simple and which can be used by lay people.

It is yet another object of the invention to provide a method for permanent hair removal that uses an alkaline solution for pretreating the hair in order to more effectively increase the conductivity of hair than is possible with known neutral or acid-based systems.

It is yet another object of the invention to provide a method of permanent hair removal by which an alkaline solution is applied to the hair to be removed for opening the cuticle and cortex layers for causing an electric power source to penetrate the hair easier and faster.

It is a still further object of the invention to provide a method of multiple hair removal by which all treated hairs slide out of their respective treated follicles with substantially no resistance.

It is another object of the invention to provide a permanent multiple hair removal method and apparatus which can be used by both professionals and non-professionals.

It is a yet still further object of the invention to provide a permanent hair removal method and apparatus which make hair removal painless.

It is still another object of the invention to provide a permanent multiple hair removal system which shortens the time required for permanent hair removal.

It is another object of the invention to provide a permanent hair removal system which is less messy than conventional systems.

It is another object of the invention to provide a permanent multiple hair removal system by which skin disorders, such as acne, can be treated concurrently with the hair removal.

It is another object of the invention to provide a permanent multiple hair removal system which uses relatively small, disposable hair removal strips.

It is another object of the invention to provide a permanent hair removal system which uses a protective, non-conductive layer of material directly adjacent the user's skin, in conjunction with a conductor or conductive layer disposed adjacent to the non-conductive layer and spaced apart from the user's skin by the non-conductive layer.

It is yet a still further object of the invention to provide a permanent hair removal system, the components of which can be applied to the user's skin in a liquid form.

It is a further object of the invention to provide a hair removal system that in one instance the hair has to be cut and in another instance left long.

It is another object of the invention to provide a multiple hair removal system which includes a multi-compound liquid which can be stored in a single container prior to use.

It is another object of the invention to provide a hair removal system, the components of which can be used for removing one hair or multiple hairs at a time.

It is a still further object of the invention to provide for multiple hair removal by the application of any one of a number of power sources or by a combination of devices with different power sources.

It is a further object of the invention to provide a substantially painless permanent multiple hair removal method and apparatus, unlike such as associated with traditional wax removal in which live hairs are pulled directly from the skin.

It is a still further object of the invention to provide for permanent multiple hair removal without the need for insertion of an electrolysis needle into the user's skin that causes burns and infection.

It is another object of the invention to provide a multi-purpose conductive pair of tweezers which functions as a conductor to a source of power, as a clamp, as a multiple-hair-removal tweezers, and as a single-hair-removal tweezers.

It is another object of the invention to provide a multi-purpose conductive comb which functions as a conductor to a source of power, as a clamp, and as a multiple-hair-removal comb.

It is another object of the invention to provide a multi-purpose hair removal device including a conductive spring which functions as a conductor to a source of power, as a clamp for directing power to a clamped hair, and as a multiple-hair-removal clamp for removing treated hairs.

It is a still further object of the invention to provide for a permanent multiple hair remover system without the need for the single tweezer method which is more time consuming.

These and further objects of the invention will become apparent from the drawings and the following description of the invention.

BRIEF DESCRIPTION OF THE DRAWINGS

FIG. 1 is a schematic cross sectional view of a section of tissue showing a typical hair;

FIG. 2 is a side elevational view of a preferred embodiment of the apparatus according to the invention when in place engaging hairs to be removed;

FIG. 3 is an elevational view similar to FIG. 2 of another preferred embodiment of the apparatus according to the invention;

FIG. 4 is a top plan view of a preferred embodiment of a conductive layer of the apparatus according to the invention;

FIG. 5 is a sectional view of the embodiment of FIG. 4, taken along line 5—5;

FIG. 6 is a top plan view of another preferred embodiment of the conductive layer of the apparatus according to the invention;

FIG. 7 is a section view of the conductive layer of FIG. 6 taken along line 7—7;

FIG. 8 is a sectional view similar to FIG. 7, of another preferred embodiment of the conductive layer according to the invention;

FIG. 9 is a somewhat schematic, exploded view of a still further preferred embodiment of a hair removal device according to the invention;

FIG. 10 is a schematic, top plan view of the preferred embodiment of FIG. 9;

FIG. 11 is a side, elevational view of the preferred embodiment of FIG. 9;

FIG. 12 is a schematic, exploded view of yet another preferred embodiment of a hair removal device according to the invention;

FIG. 18 is a perspective view of a preferred embodiment of a conductive hair removal comb according to the invention;

FIG. 19 is a side, elevational view of the hair removal comb of FIG. 18;

FIG. 21 is a partial, side view of FIG. 20, when the hair removal comb is open, and hairs to be removed extend freely through the comb;

FIG. 22 is a partial, side view of the comb as shown in FIG. 21, with hairs to be removed shown clamped by the teeth of the comb;

Figure 13:
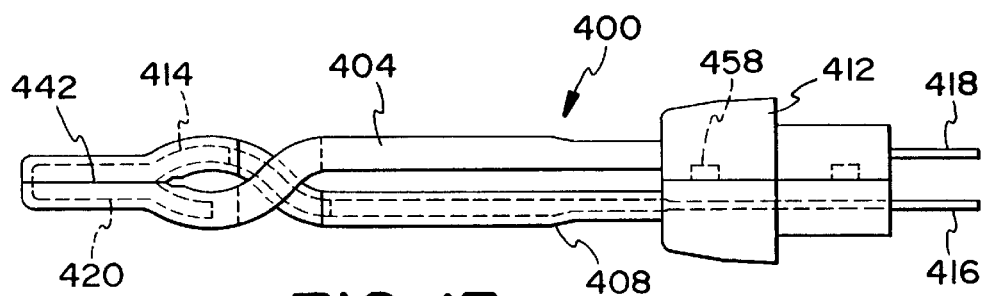
FIG. 13 is a top plan view of a preferred embodiment of conductive tweezers according to a preferred embodiment of the invention.

It should be understood that all hair removal embodiments according to the invention can be used with all electrical power sources: e.g., radio frequency (RF), direct current (DC), blend (i.e., DC+RF), and alternating current (AC) systems.

DETAILED DESCRIPTION OF THE INVENTION

FIG. 1 is a representation of the manner in which hair is typically found. A hair 10 includes an upper shaft portion 12, which extends above a skin surface 13, and an interior lower shaft portion 14 extending beneath skin surface 13. Hair 10 passes adjacent to oil glands 16 disposed immediately below an epidermis area 18. Lower shaft 14 is connected to an external root sheath layer 20. The growth site for hair 10 is located in a matrix area 22. Matrix area 22 contains a papilla 24 supplied with nutrients by a blood vessel 26. Matrix area 22 and the cells 23 surrounding the follicle are the parts which must be reached and destroyed by electrical or chemical energy or heat energy if future hair growth is to be prevented, given that all of the cells of the hair 10 above matrix area 22 is substantially dead fibrous material.

Accordingly, the target for an electrical current to be applied to hair 10 is essentially papilla 24, matrix area 22, and adjacent cellular structures.

It has been found that substantially dry hair 10 is not a sufficiently good electrical conductor for the present purposes. Hair becomes a better conductor when moisture is allowed to be absorbed into the hair shaft so that an electrical current and/or heat energy can be induced. Then electrical current and/or heat energy can be conducted from inner upper portion 12 to inner lower shaft portion 14 and, hence, the area around matrix 22.

FIG. 2 shows a preferred embodiment of a multiple hair removal device 50 according to the invention that can carry out the multiple hair removal method according to the invention. Hair removal device 50 includes a non-conductive or conductive glue, adhesive, or wax layer 52, a non-conductive, adhesive, plastic, or wax layer 53, a structural layer 54, and a conductor or conductive layer 56 disposed therebetween. It is expected that layer 53 disposed adjacent the skin, in use, may be minimally conductive so as to not cause a shock or burn to the user's skin. Conductive layer 56 is connected to a power source 70 by means of a power transmission cable 72 or by a clamping means.

Turning to FIG. 3, a still further preferred embodiment of the an apparatus according to the invention is shown as a multiple hair removal device 80. Multiple hair removal device 80 includes a conductive wax, glue, or similar adhesive material defining a conductive layer 82 which includes an adhesive material 84 and electrically conductive material or particles 86 embedded in and dispersed throughout adhesive material 84.

A separate non-conductive layer 85, for placement directly on the skin, is provided in this embodiment. It is expected that layer 85 disposed adjacent the skin, in use, may be minimally conductive so as to not cause a shock or burn to the user's skin.

Adhesive material 84 is selected from compounds which adhere to human hair. Layer 82 is made of conducting material or rendered conductive by the presence of conductive particles 86. An optional structural layer 88 is disposed on top of and adhered to conductive layer 82. Power transmission cable or electrode 72 or clamping means is associated with conductive layer 82 for transmitting power from power source 70.

FIGS. 4 and 5 illustrates a preferred embodiment of a conductive layer 90 for use with the multiple hair removal device such as shown in FIG. 2, when power source 70 is any electrical source. It is expected that an RF (radio frequency) power source be operatively associated with conducted layer 90, for example. Accordingly, RF focusing areas 92 are provided that serve as focal points at which the RF power is intensified. For other electric sources, such as alternating current (AC), direct current (DC), or DC-biased RF (so-called "blend"), the flat configuration pad makes this embodiment a multiple use conductor.

FIG. 5 illustrates that the configuration of RF focusing areas 92 allow for conductive layer 90 to be substantially flat and foil-like, yet with sharp edges at which the RF is intensified, for example.

FIGS. 6 and 7 show another preferred embodiment of a conductive layer 100 having attachment tabs 102 that may be used in a multiple hair removal device similar to that shown in the preferred embodiment of FIG. 2. Attachment tabs 102 are used for being attached to a power source by conductive releasable attachment members such as so-called "alligator clips" or tweezers such as described in detail below and shown in FIGS. 13–17. FIG. 7 is a sectional view of FIG. 6 illustrating electrical focusing points 104 which serve as intensifiers and directors for electric power applied to tabs 102. For example, focusing points 104 direct AC or DC, and intensify RF power.

FIG. 8 illustrates a still further embodiment of a conductive layer 110 made of a conductive plastic material and which can be used in hair removal device such as shown in FIG. 2.

Turning to FIGS. 9–11, another preferred embodiment of a hair removal device 200 according to the invention is illustrated. Hair removal device 200 includes a vinyl layer 204, such as a top of an envelope for protecting the operative elements of hair removal device 200 during storage. A conductive layer or conductor 208 includes one or more pull tabs 210, 212, both of which likewise function as conductor leads when in use.

A conductive layer 214 is disposed adjacent conductor 208 and between a non-conductive layer 218 and conductor 208. Non-conductive layer 218 is made of material engineered to removably adhere to the user's skin and to allow hair to penetrate therethrough. A vinyl layer 222 functions as the bottom of a protective envelope including vinyl layer 204, both of which collectively protect conductor 208, conductive layer 214, and non-conductive layer 218 when hair removal device 200 is being stored.

The invention can be carried out with conductor 208, conductive layer 214, and non-conductive layer 218. Still further, it is possible to use just conductive layer 214 and non-conductive layer 218 to achieve the objects of the invention.

As best seen in FIG. 10, a perforation 232 is provided to ensure that vinyl layers 204 and 222 are cleanly separated and removed when one or more of pull tabs 210, 212, and 226 are used.

FIG. 12 shows a yet still further embodiment of a hair removal device 300 according to the invention, which has been shown on an exaggerated, exploded view for clarity.

Hair removal device 300 includes a vinyl layer 304 functioning as the top of a protective envelope, a conductor or conductive layer 308 having a pull tab 310 which likewise functions as a conductor lead and, preferably, a second pull tab 312. A conductive layer 314 is disposed between conductor 308 and non-conductive layer 318. A second vinyl layer 322 serves as the bottom of an envelope when joined with top vinyl layer 304, in a manner similar to the embodiment of FIGS. 9–11.

Preferably, a pull tab 326 is provided on vinyl layer 322 for assisting in the separation of vinyl layers 304 and 322 when the hair removal device is to be used.

A hole 334 defined in vinyl layer 304 aligns with an aperture 338 in conductor layer 308, which aperture 308 in turn aligns with a throughhole 342 in conductive layer 314. A further aperture 346 disposed in non-conductive layer 318 is likewise aligned with a hole 350 formed in lower vinyl layer 322. Holes 334 and 350 are optional. This special annular shape is useful when a woman wishes to remove hair around the areola resulting from hormonal changes induced by birth control pills, for example. The respective holes are configured for placement over a woman's nipple to avoid contact with the sensitive skin thereof.

Turning to FIGS. 13–17, various insulated pairs of tweezers or tongs 400 according to additional preferred embodiments of the invention are illustrated.

FIG. 13 shows that insulated tweezers 400 preferably include an upper arm 404 normally biased against a lower arm 408. The terms "upper" and "lower" are used for expedience as the terms describe the relationship of arms 404 and 408 as viewed in FIG. 13, and are not intended to be limiting.

A base 412 is configured for insertion into a casing described below with regard to FIG. 17, for example.

A metal insert 414 extends substantially along almost the entire length of lower arm 408 and terminates in a free end or conductive extension 416. An opposed extension 418 can be made of metal or plastic, depending upon the intended use, as will be apparent from the description of the operation of tweezers 400 below.

A conductive metal insert 420 extends along only a part of the length of upper arm 404, as the illustrated pair of tweezers 400 is engineered for use with DC, RF, or DC-biased RF power sources.

Figure 14:
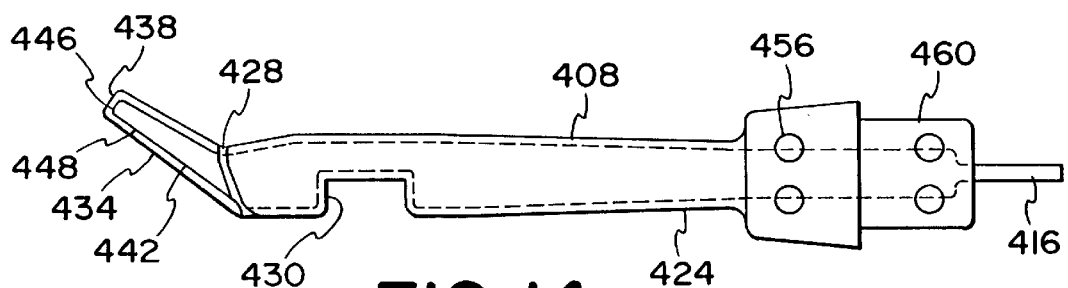
FIG. 14 is a side elevational view of one arm of the pair of tweezers of the preferred embodiment of FIG. 13.

As best seen in FIG. 14, lower arm 408 includes a plastic casing 424 which substantially completely surrounds metal insert 414.

As best seen in FIG. 14 an optional stepped portion 428 of plastic casing 424 demarcates a hair-grasping end 434 of arm 408. A "single" hair grasping free end 438 is defined at an outermost portion of hair-grasping end 434. A hair-contacting portion 442 of metal insert 414 is left partially uncovered by plastic casing 424.

Referring to both FIGS. 13 and 14, one can see that when tweezers 400 are in their normally closed position, hair-contacting portions 442 of opposed tweezer arms 404 and 408 will make contact. In use, hair-contacting portions 442 grasp respective portions of hairs to be treated. Hair-contacting portion 442 has a sufficiently short width at a "single" —hair contacting end 446 that one or two hairs can be conveniently grasped.

A multiple-hair grasping portion 448 of hair-contacting portion 442 is sufficient long that multiple hairs can be grasped at the same time. Single-hair contacting portion 446 is surrounded by insulating material at 438 and elsewhere, so that exposed portion 442 will not contact the user's skin. Likewise, exposed portion 442 is set back from the free edge of insulating plastic casing 424 in the region of multiple-hair contacting region 448 so that the skin is not contacted by exposed portion 442; rather, only the hairs to be treated are grasped and contacted by exposed portion 442. One or more alignment bosses 456 are provided on lower arm 408 for mating with respective seats 458 disposed in arm 404.

A stepped base portion 460 extends from base 412.

Figure 16:
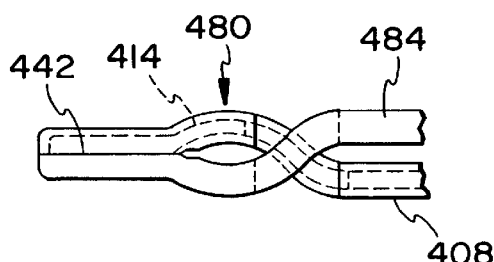
FIG. 16 is a top plan view of still another preferred embodiment of conductive tweezers according to a preferred embodiment of the invention.
Figure 15:
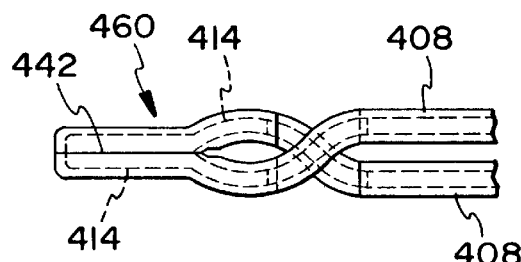
FIG. 15 is a top plan view of another preferred embodiment of conductive tweezers according to a preferred embodiment of the invention.

FIGS. 15 and 16 show additional embodiments, depending on the intended power source and particular application, of insulated tweezers similar to insulated tweezers 400 of FIG. 13. The FIG. 15 tweezers 460 have two opposing arms, each of which have full length conductive metal inserts 414 therein. The FIG. 16 embodiment of a tweezers 480 has two opposing arms, one of which has a full length conductive insert 414, with no metal insert at all in an opposed arm 484; for example.

Each one of upper arm 404 and lower arm 408 of the embodiment of FIG. 13, as well as each of the opposed arms of the embodiment of FIGS. 15 and 16, such as non-conductive arm 484, may be detachably attached to base 412.

Figure 17:
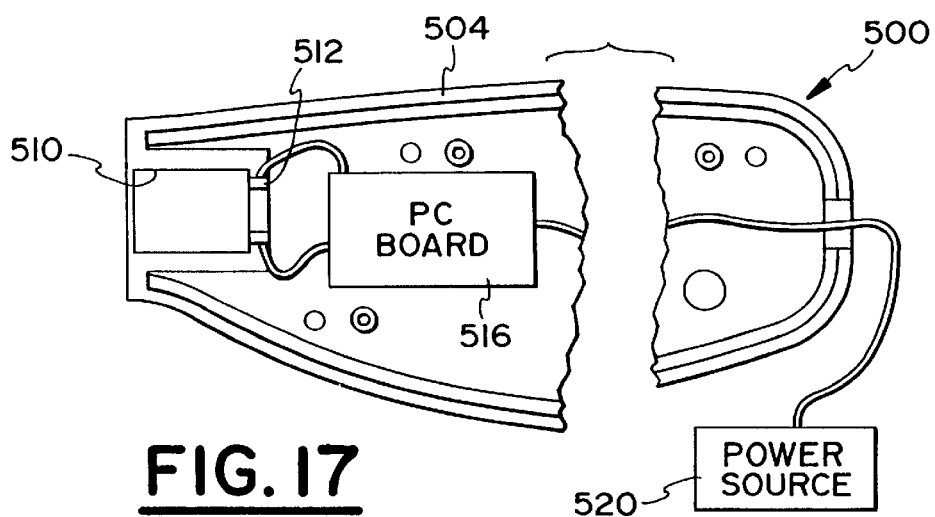
FIG. 17 is a top plan view of one half of a hand-held casing according to a preferred embodiment of the invention suitable for retaining and powering the various pairs of tweezers of the embodiments of FIGS. 13–16.
Figure 27:
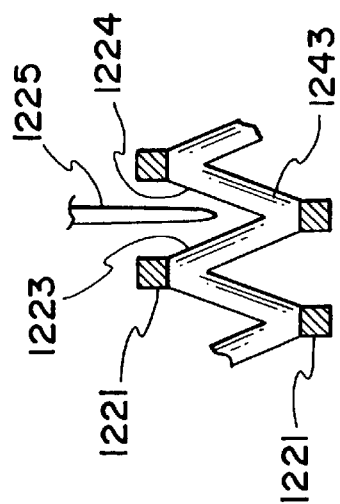
FIG. 27 is an enlarged view of a portion of the device of FIG. ig. 23.

FIG. 17 illustrates a hand-held casing 500 which is used for securing and powering insulated tweezers 400 of FIGS. 13–16. Hand-held casing 500 includes a plastic case 504 and a tweezers receptacle 510 configured for receiving stepped based portion 460. One or more female connectors 512 receive conductive extension 416 and extension 418. A conventional printed circuit (PC) board 516 converts and regulates the power supplied by a standard power source 520 into the desired type of power used in the hair removal system selected according to the invention, such as AC, DC, DC-biased RF, and the like, as described above.

FIGS. 18–22 illustrate hair clamping combs according to further preferred embodiments of the invention.

The preferred embodiment of a hair clamping comb 600 having a base 612. Clamping comb 600 includes a lower, toothed comb 606 having a plurality of teeth 608. A further comb 610 having a plurality of teeth 611 is provided between lower comb 606 and a movable clamp 615. Movable clamp 615 is conveniently provided with an extension 624 against which an operator can apply force for rotating clamp 615 about a pivot 626 in the direction of arrow 630. Comb 600 will be spring-biased in a normally closed position (i.e., the position shown in FIG. 19) or in a normally open position (the position shown in FIG. 18) depending on the intended use and the intended power source, for example. Lower comb 606 will typically be made of non-conductive, insulating plastic, as will be the plurality of teeth 608 thereon. Central comb 610 will typically be made of a conductive metal. At least the teeth 611 thereof will generally be made of a conductive metal. Such metal teeth 611 will be electrically connected with a free end or conductive extension 616. An opposed extension 618 will be made of metal or plastic, depending upon the intended use, as will be readily apparent from the description of the use of hair treatment devices under OPERATION below.

A conductive metal insert 620 is provided in a portion of clamp 615. An outer, insulating portion 622 of clamp 615 covers metal insert 620 for preventing a user from contacting metal insert 620 when in use. As will be appreciated, metal insert 620 will be sufficiently large to contact at least a portion of the ones of metal sheet 611 which will be actively used in hair removal.

A representative hair 644 is shown clamped between a representative tooth 651 and metal insert 620 when hair 651 is being treated for removal. In use, a plurality of hairs will be clamped at one time.

A stepped base portion 660 extends from base 612 and is configured for being inserted into receptacle 510 of hand-held casing 500 shown in FIG. 17.

Figure 20:
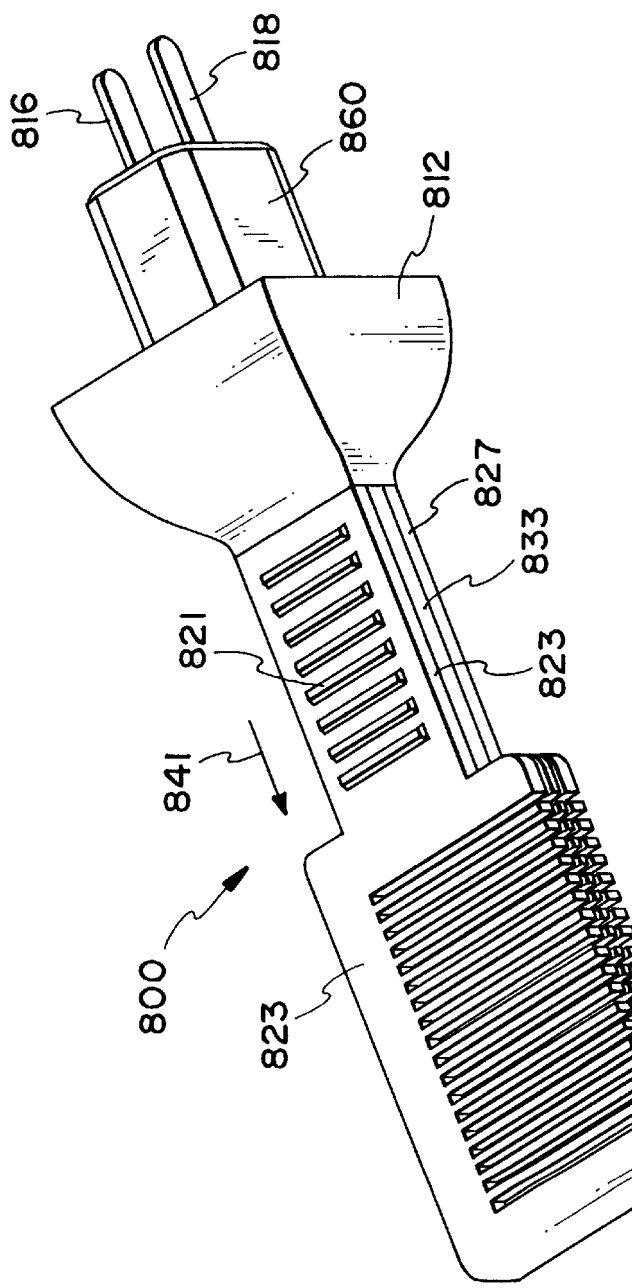
FIG. 20 is a perspective view of a further preferred embodiment of a hair removal comb according to the invention.
Figure 23:
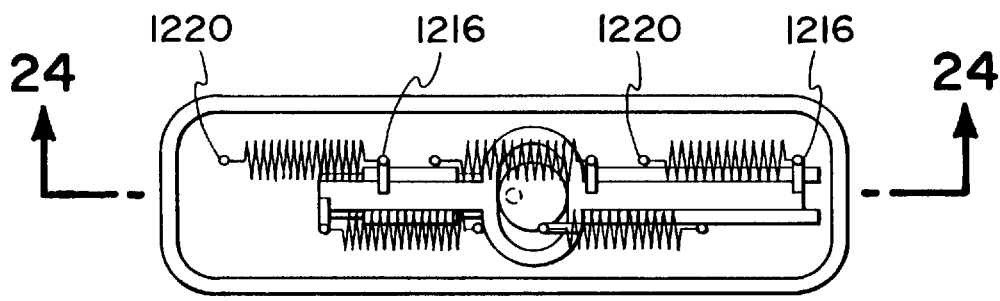
FIG. 23 is a top view of a further hair removal device according to the invention.
Figure 24:
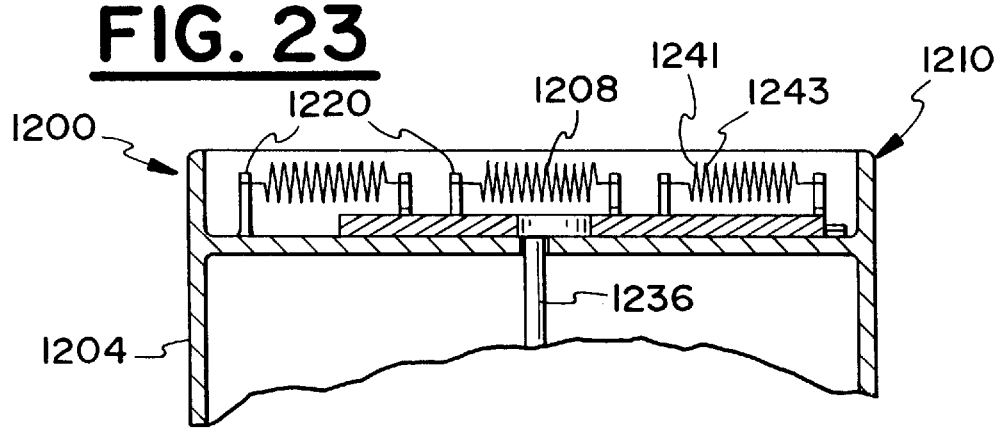
FIG. 24 is a partial elevational view of the hair removal device of FIG. 23, taken along line 24—24 therein.
Figure 25:
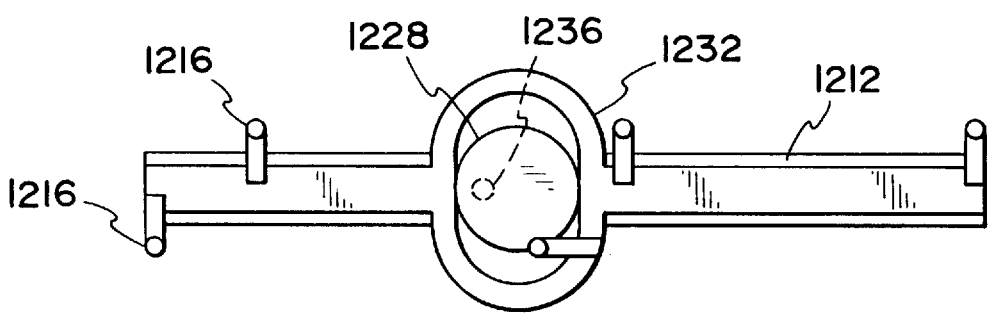
FIG. 25 is a top view of a slider element according to the invention.
Figure 26:
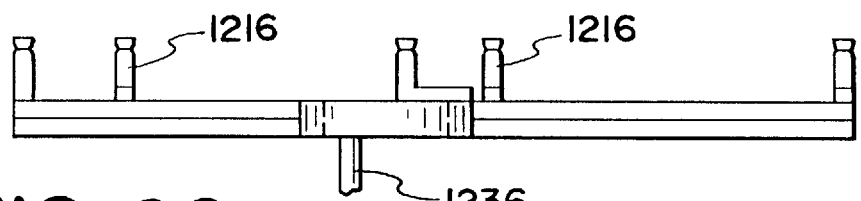
FIG. 26 is an elevational view of the slider element of FIG. 25.

Turning to FIGS. 20–22, the further preferred embodiment of a hair removal comb 800 according to the invention is illustrated.

Hair removal comb 800 includes a base 812 having a conductive extension 816 and a further extension 818, which can be conductive, depending on the power source selected. One or more protrusions 821 are provided on an outer face of an upper comb 823. Protrusions 821 are preferably sized sufficiently large so as to be easily engaged, pushed, and pulled by one or more of a user's fingers. Upper comb 823 will typically be provided with a conductive metal insert 825. A lower comb 827 will typically be a non-conductive, insulating material, as such lower comb 827 will be used adjacent to the client's skin 831. A central comb 833 will typically be made of a conductive metal material. For most purposes, conductive central comb 833 will be electrically connected with conductive extension 816.

FIG. 21 illustrates a plurality of hairs 837 extending between adjacent ones of substantially aligned teeth of respective combs 823, 833, and 827.

Conventional, unillustrated guides serving as sliding elements allows upper comb 823 to be slid relative to central comb 833 in the direction of arrow 841 when a force is provided in the direction of arrow 841 on protrusions 821, for example. Conveniently, upper comb 823 and lower comb 827 can be made of a single piece of insulating material, so that lower comb 827 moves therewith. Owing to the movement of upper comb 823 relative to central comb 833, portions of metal insert 825 will engage hairs 837 and establish electrical contact with conductive metal central comb 833. For example, a portion 851 of metal insert 825 will press against and firmly engage hair 837 with a portion 853 (such as a portion of the comb tooth) of central comb 833. The power source will then be actuated for a predetermined period of time, and the clamped hairs 837 will be immediately removed by movement of comb 800 away from skin 831, or hairs 837 will be released for later removal, depending on the power source used, as described elsewhere.

FIGS. 23–27 illustrate a preferred embodiment of a hair treatment or hair plucker attachment 1200 according to the invention. Hair plucker attachment 1200 includes a snap-on body 1204 which is configured to releasably engage the hand-held casing 500 of FIG. 17, in the same manner as the attachments of the embodiments of FIGS. 13–22. A plurality of springs 1208 is disposed adjacent an outer free end 1210 for engaging hairs on a user's body to be treated. A slider 1212 is movably mounted on body 1204 and includes slider posts 1216 which move therewith.

A plurality of fixed posts 1220 is disposed on body 1204.

A cam 1228 drives a cam follower 1232 for thereby imparting a reciprocatory motion to slider 1212. A cam shaft 1236 attached to and extending from cam 1228 is configured for engaging a mating driven member for powering hair treating attachment 1200, such as by being coupled to an unillustrated drive shaft of a motor. As will be readily appreciated, when cam shaft 1236 is rotated, the rotation of cam 1228 causes slider 1212 to reciprocate, whereby slider posts 1216 move back-and-forth relative to fixed posts 1220. Given that each one of springs 1208 has its respective free ends connected to ones of slider posts 1216 and fixed posts 1220, the reciprocatory movement causes springs 1208 to open and close. This opening and closing of springs 1208 causes springs 1208 to alternately grab and release hairs on the body of a user when hair treating attachment 1200 is in use.

Springs 1208 may be provided with an insulating material 1221 which has been applied on the outer faces thereof, such as when the springs are in a fully closed position (i.e., no gap between adjacent coils 1241 and 1243 of spring 1208). Contacting faces 1223 and 1224 are substantially free of insulation. In that manner, springs 1208 can be used to grasp hair, and the appropriate power source will be applied as in the previous embodiments and an insulating layer of material will be disposed adjacent the user's skin when spring 1208 is closed and the electrical power source is being applied therethrough to the hair clamped between adjacent coils 1241 and 1243, thereby clamping a hair 1225, for example. One or more of springs 1208 is electrically connected to a conductive extension, such as in the embodiments of FIGS. 13–22. It is likewise contemplated that a timer will be provided for determining the length of time the springs 1208 are in the closed position (i.e., coils 1241 and 1243 are pressed adjacent each other, such as when clamping a piece of hair) and/or the length of time the power source is being applied to spring 1208 for directing power to a treated hair. There may likewise be provided an audible or visible alarm, such as a buzzer or light, respectively, so that the user knows that the power has been supplied for a sufficiently long period of time to treat the clamped hair and/or so that the user knows that springs 1208 are being powered. Accordingly, when in use, an elegantly simple solution to the problem of treating and removing hair from the user's body has been achieved. Namely, as cam shaft 1236 is being driven for opening and closing springs 1208, the user simply slides free end 1210 along the surface of the user's body, whereby hairs are grabbed and, owing to the movement of hair treating attachment 1200 by the user, the hairs are removed during the phase in which springs 1208 are closed.

It is likewise contemplated that additional reciprocatory movements be imparted to the opening and closing springs, such as by a mechanical movement which opens some of the springs at the same time others of the springs are being closed.

Furthermore, it is contemplated that a different slider and spring openings/closing mechanism be used so that after the springs have been closed, movement is imparted to the closed springs, so that the movement of the closed springs relative to the user's body causes a grasped hair to be removed, as opposed to the movement of the user's hand causing the removal of the unwanted hair.

Figure 28:
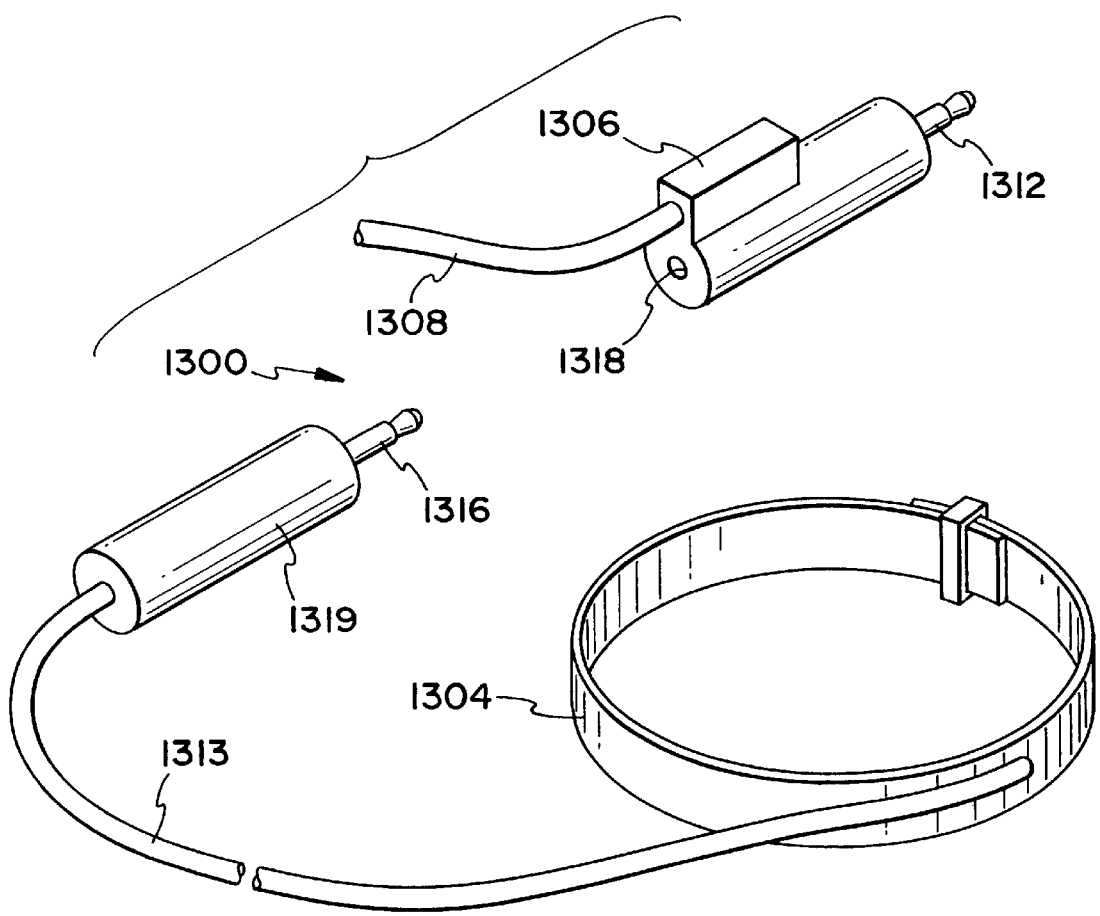
FIG. 28 is a perspective view of a direct current (DC) grounding unit according to the invention.

FIG. 28 illustrates a grounding accessory 1300 for use with all the hair removal embodiments of the invention, in the case where a DC power source is being used. When the person whose hair is being removed is working on himself or herself (e.g. the "patient" is the "user") the DC grounding accessory 1300 is unnecessary, as the patient will be inherently grounded. When an operator of one of the DC power source accessories described above is someone other than the person whose hair is being removed, DC power source accessory 1300 will be used. A grounding strap 1304 is provided, which may conveniently be used as a wrist strap. If the patient being worked on holds the strap 1304 in his or her hand, sufficient grounding will typically be achieved. A power source piggy back connector 1306 includes an electrical connector 1308 which will be attached to the conventional transformer or other power source, in use. Piggy back connector 1306 includes a male connector 1312 which will be attached to the accessory being used (e.g., male connector 1312 will plug into a mating female receptacle in the casing of the hair treating devices described above). A grounding cable 1313 extends from grounding strap 1304 and electrically connects to a male connector 1316. A connector body 1319 is grasped by the user when male connector 1316 is inserted into female connector 1318 of piggy back connector 1306 when grounding strap 1304 is used.

OPERATION

The preferred embodiment of the method of permanently removing one or more hairs according to the invention will become more apparent by first considering the manner in which the embodiments of the apparatus shown in FIGS. 2–7 are used.

Multiple hair removal device 50 of FIG. 2 is used as follows. Preferably, the skin having hair to be treated and removed is first steamed in order to both open the pores and to moisturize the hair for enhancing conductivity thereof. A conductive solution, which may be a liquid, a gel, an emulsion, or a cream, is applied to the hair. The conductive solution is left in contact with the hair for a predetermined period of time. Preferably, the conductive solution has an alkaline formulation and a pH in the range of about 9 to 11. The length of the predetermined period of time is determined as described below, then the solution is wiped off.

Multiple hair removal device 50 is then pressed against the skin surface to be treated, ensuring that non-conductive adhesive layer 53 is closest to skin surface 13. Upper portion 12 of the hair to be removed extends through non-conductive adhesive layer 53 and contacts adhesive conductive layer 52 as multiple hair removal device 50 is pressed against the skin. Thus, hair 10 itself serves as a path by which power is transmitted from conductive source to matrix root area 22 of the hairs to be destroyed. Some or all of hairs 12 may directly contact conductor 56.

Power source 70 is then turned on for a predetermined length of time. The predetermined period of time is a function of the area of the hair to be treated, the number of hairs to be destroyed, the physical attributes of the hair, the type of power source being used, and like considerations. Accordingly, it is preferred that a preliminary test be done because the length of time required varies not only from person to person, but from one area of the body to another. Advantageously, a test area, commonly known as a "patch test" is done as it serves the additional purpose of determining whether the user is allergic to the conductive solution or to other constituents, such as the adhesive layer and how well the roots and hair accepts the treatment.

After the application of power to kill the hair, the destroyed hair is allowed to remain in the body for a predetermined period of time, inasmuch as a chemical reaction has been started in the vicinity of matrix area 22 by the application of power thereto, and the chemical reaction continues at this site of hair growth for a period of time. This is typically done only with the DC unit.

For a fuller discussion of the chemical processes which are involved, attention is directed to U.S. Pat. No. 4,174,714 to Mehl U.S. Pat. No. 5,049,148 to Mehl, U.S. Pat. No. 5,364,394 to Mehl, and U.S. Pat. No. 5,026,369 Cole described above, each of which is incorporated herein by reference.

In order to optimize the length of time for which power is applied, one can conduct a test of the removed hairs so as to gauge the amount of destruction of matrix area 22. This is typically done only with DC unit.

This test is accomplished by use of a standard piece of litmus paper and distilled or deionized water. The piece of litmus paper is placed on the test bench, a drop of distilled and/or deionized water is applied, and the matrix area 22 of a removed hair is touched to the surface of the litmus paper. A destroyed matrix area 22 will have undergone a chemical change sufficient that a spot on the piece of litmus paper to which matrix area 22 was touched indicates a pH in the range of about 9 or greater. If the pH registers lower than about 9, then the user simply increases the period of time for which power is applied.

The litmus test is repeated as required to determine the length of time necessary to properly treat a given body area of hair. After the proper length of time for the application of power has been determined, a larger area of the same part of the body can be treated by simply multiplying the length of time the power has been applied to the test area by the ratio of the size of the larger area to be treated to the size of the test area. For example, if one minute was required for properly treating one square inch of hair, then ten minutes would be required for treating ten square inches of the same type of hair.

Preferably, the hair to be removed is substantially uniform and relatively short.

If the hair is not short then it is preferred that the hair be cut in the area to be treated. If it is necessary to shave off the hair, the user's hair should be allowed to grow for about three days so as to achieve a substantially uniform, relatively rigid stubble.

These relatively short and rigid hairs have been found to extend well through non-conductive layer 53 and into conductive adhesive or wax layer 52 for contacting conductive layer 56. This length of hair after about three days growth has likewise been found to ensure that there is sufficient contact area between upper shaft portion 12 of hair 10 and conductive adhesive layer 52 so that the treated hair can be removed.

It is further preferred that in the case of adhesive layer 52 being made of a wax-like substance, layer 52 is pressed in the direction opposite to normal hair growth. After treatment, the hairs having destroyed matrix areas 22 are removed in the opposite direction; namely, in the direction of normal hair growth.

The embodiments of the multiple hair removal device as shown in FIGS. 3–8 are used in a similar fashion. Conveniently, conductive layer 100 of FIG. 6 has tabs 102 to which a readily removable power source can be clamped, for example, as by alligator clips.

Likewise, the embodiments of FIGS. 9–12 are used to remove multiple hairs in a manner similar to the use of the above embodiments.

Tweezers 400 of FIGS. 13 and 14, as well as tweezers 470 and 480 of FIGS. 15 and 16, respectively, are engineered to be used in multiple ways.

When using the embodiments of FIGS. 9–12, for example, tweezers 400 serve as power connectors and are attached to conductive pull tabs 210 and 212 in a manner similar to traditional normally closed alligator clips. When tweezers 400 are used to supply power, tweezers 400 can be inserted into hand-held casing 500 by mating extensions 416 and 418 with female connectors 512 as stepped base 460 engages tweezer receptacle 510. Power source 520 then supplies the required power to conductive extension 416, for example, the required power having been determined by PC board 516. The power selected for the particular method is transmitted through metal insert 414 and through exposed portion 442 for supplying power to conductive tabs 210 and 212 of the preferred embodiment of FIG. 9, for example.

If any hairs remain after performing the multiple hair removal treatment methods described above, tweezers 400 and casing 500 of FIGS. 13–15 can be used as a separate operating component of the overall hair removal system. In that case, tweezers 400 will be used to grab single or multiple hairs extending from the user's skin directly after the appropriate steps of applying conductive solutions have been carried out as described above. To open normally closed hair-grasping end 434, the user presses upper arm 404 toward lower arm 408 whereby the arms move relative to each other, facilitated by detent 430. Tweezers 400 are placed against the skin so that hair-grasping end 434 is near to the hairs to be removed. The plastic casing 424 defines the non-conductive regions surrounding exposed metal hair contacting portion 442; namely, a power transmission area is thereby defined.

The preferred embodiments of FIGS. 18–28 will be used as described above.

The preferred sources of power include DC power, radio frequency power, galvanic thermolysis, and combinations thereof, such as DC-biased RF or blend.

The length of time during which the hair is allowed to stay in the body after the power has been treated varies and is preferably about 30 minutes for DC or galvanic method. This time is believed to be adequate for the chemical reaction which has been induced by the application of power at matrix area 22 to continue sufficiently long for the so-called galvanic effect to take place, thereby leading to permanent impairment of future hair growth.

RF, thermolysis, and DC-biased RF or blend treated hairs can be removed immediately after treatment.

The above method effectively removes all treated hairs at this stage of growth. In order to get complete and permanent hair removal, the above method steps will be repeated when the user can see hair stubble in the treated area resulting from hairs at different growth stages not removed by the first treatment. Additional treatments may be required as new hair growth occurs that may be induced by hormonal changes and the user's life cycle.

The preferred materials for the non-conductive and conductive layers include adhesives, glues, and hot or cold waxes, and conductive particles, as required, for conductivity. The conductive layer may be made of conductive metals, conductive plastics, and thin foils of those materials or ceramics.

It is also contemplated that the material of the conductive layer will be selected so that it changes color over time. Thus, exposure to air, exposure to the contacted user's skin (such as by a reaction to the warmth, moisture, and/or pH of the skin), or even exposure to the hair itself will cause a color change in the conductive layer. The color change tells the user useful information such as: the conductive layer material has been on the skin for a sufficient period of time so as to provide a visual indication to the user that the conductive material may be removed, given that the period of time suffices for fully treating the hair to be removed.

It is likewise contemplated that the material of the conductive layer or wax will be selected so that the color of the conductive layer changes as a function of the electric current or other power applied thereto. In that way the user gets visual confirmation that sufficient electrical power and/or electrical power for a sufficiently long period of time has been applied to the conductive material so as to fully treat the hair to be removed.

The configuration of the conductor layer may be changed in order to heighten the effects of a particular power source, provide tabs for attachment to a power source, or to treat specific shapes of the body.

Different sizes of the multiple hair removal devices may be used depending on body area and whether the intended use is for an initial treatment when the removal of large numbers of hairs is required, or smaller devices covering reduced areas of the skin may be used when follow-up treatments are performed or when only a small area of the skin is to be treated. Curved configurations may be used for application to the user's eye brow area or larger square. Round or oblong shapes for arms, legs, or any large area are likewise contemplated.

It is also contemplated that the non-conductive layer of material disposed directly adjacent the user's skin will be supplied in a liquid form which is applied by the user to the area of the user's skin be treated while the material is still liquid. After a period of time, the liquid will dry sufficiently on the user's skin so that a non-conductive semi-solid or solid layer is achieved. Likewise, the conductive layer disposed adjacent the non-conductive layer, and separated from the user's skin by the non-conductive layer, will be applied in a liquid form, and allowed to dry, as necessary. A third layer, such as the conductor layer of some of the preferred embodiments of the invention, will also be applied in liquid form on top of the conductive layer, and be allowed to sufficiently dry, as required.

It is likewise contemplated that the two or more liquid materials described in the previous paragraph will be supplied in a single liquid-retaining container, whereby the user simply shakes the container prior to use, applies all three liquids at the same time by use of an applicator, and the two or three liquid materials separate prior to hardening. In this manner, all the layers will be applied at once in a liquid form with only one liquid application step.

In the case of two or three liquids in one container, the liquids will preferably be immiscible, and the lowermost, nonconductive material will be heaviest, so that it sinks to the lowermost point and, in use, contacts the skin.

While this invention has been described as having preferred designs, it is understood that it is capable of further modifications, uses and/or adaptations of the invention following in general the principle of the invention and including such departures from the present disclosure as come within the known or customary practice in the art to which to invention pertains and as may be applied to the central features hereinbefore set forth, and fall within the scope of the invention and of the limits of the appended claims.

What is claimed is:

1. A method of removing hair comprising the steps of:
   a) applying a conductive solution to a skin surface of a skin to be treated;
   b) engaging hairs to be removed from the skin with a toothed comb having a conductive element therein;
   c) applying power from a power source through the conductive element of the comb and to the hairs to be removed from the skin;
   d) said step of applying power being carried out for a period of time sufficiently long to induce a chemical reaction in the matrix area of the hairs to be removed;
   e) allowing the hairs to remain in the skin for a period of time sufficiently long so that the chemical reaction induced in the previous step continues sufficiently long for destroying the matrix area of the hair; and
   f) removing the hairs.

2. A method of removing hair as defined in claim 1, wherein:
   a) said step of applying power includes treating the hairs with blend.

3. A method of removing hair as defined in claim 1, including the steps of:
   a) reducing the length of the hair to be removed by shaving the hair close to the skin; and
   b) providing for substantially about three days of hair growth time for the hairs shaved in said step of reducing the length of the hair before performing the remaining steps of removing hairs.

4. A method of removing hair as defined in claim 1, including the steps of:

a) applying DC in said step of applying power;

b) removing one of the hairs killed in the previous steps; and c) conducting a litmus paper test to determine the desired length of time required for applying power in the power application step by touching the matrix area of the removed hair to a wetted piece of litmus paper.

5. A method of removing hair as defined in claim 1, including the step of:

a) steaming the skin to be treated prior to the application of the conductive solution for opening the pores in the skin.

6. A method of removing hair as defined in claim 1, further including:

a) providing the toothed comb with a movable clamp; and b) said step of removing the hairs includes clamping the treated hairs with teeth of the comb and the movable clamp, and then moving the comb with hair clamped therein relative to the skin.

7. A method of removing hair as defined in claim 1, wherein:

a) said step of applying power includes treating the hairs with DC.

8. A method of removing hair as defined in claim 1, wherein:

a) said step of applying power includes treating the hairs with thermolysis.

9. A method of removing hair as defined in claim 1, wherein:

a) said step of applying power includes treating the hairs with RF.

10. A method of removing hair as defined in claim 1, further including:

a) reducing the length of the hairs to be removed by cutting the hairs to be removed prior to said step of removing the hairs.

11. A method of removing hair as defined in claim 1, wherein:

a) the toothed comb provided in said step of engaging hairs to be removed with a toothed comb includes a movable portion movable relative to a fixed portion; and b) said step of engaging hairs to be removed includes moving the movable portion relative to the fixed portion for engaging hairs therebetween.

12. A hair removal comb, said comb including:

a) a comb member having a plurality of teeth;

b) at least one of said plurality of teeth including a conductive portion therein, and said conductive portion being connectable to a power source;

c) a non-conductive element disposed adjacent to and spaced from said conductive portion;

d) said conductive portion and said non-conductive element defining a power transmission area;

e) said power transmission area being sufficiently large for contacting a plurality of hairs; and f) at least a part of said conductive portion and at least a part of said non-conductive element being configured for engaging at least one of a plurality of hairs when in use.

13. A hair removal comb as defined in claim 12, wherein:

a) a further conductive portion is provided within said non-conductive portion.

14. A hair removal comb as defined in claim 12, wherein:

a) said comb member includes a movable element and a fixed element, said movable element being movable relative to said fixed element for engaging hairs extending therebetween.

15. A hair removal comb as defined in claim 14, wherein:

a) said movable element includes a clamp.

16. A hair removal comb as defined in claim 15, wherein:

a) said clamp includes a spring-loaded clamp; and b) said spring-loaded clamp includes an extension which normally engages at least one of said plurality of teeth.

17. A hair removal comb as defined in claim 15, wherein:

a) said clamp includes a spring-loaded clamp; and b) said spring-loaded clamp includes an extension which is normally disengaged from said plurality of teeth.

18. A hair removal comb as defined in claim 16, wherein:

a) said movable element includes said conductive portion.

19. A hair removal comb as defined in claim 15, wherein:

a) said movable element includes said conductive portion.

20. A hair removal comb as defined in claim 14, wherein:

a) said movable element includes said conductive portion.

* * * * *